US00PP28943P2

(12) United States Plant Patent
Van Swieten

(10) Patent No.: US PP28,943 P2
(45) Date of Patent: Feb. 6, 2018

(54) ***PHALAENOPSIS* ORCHID PLANT NAMED 'PHALDUXHA'**

(50) Latin Name: ***Phalaenopsis* hybrid**
Varietal Denomination: PHALDUXHA

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 8 days.

(21) Appl. No.: 14/999,883

(22) Filed: Jul. 13, 2016

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

(56) References Cited

PUBLICATIONS

UPOV-PLUTO Plant Variety Database, citation for 'PHALDUXHA' Sep. 6, 2017.*
EU Community Plant Variety Rights Application No. 2015/2222, Application n°A201501719, filed Sep. 24, 2015, 8 pages.
EU Community Plant Variety Office Official Gazette, 6.2015, Dec. 15, 2015, cover page and pages 36, 55.

* cited by examiner

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALDUXHA', particularly characterized by having white flowers, 1 to 4 peduncles that are long and sturdy, leaves that are obovate, and is propagated by meristem tissue culture, is disclosed.

3 Drawing Sheets

Genus and species: *Phalaenopsis* hybrid.
Variety denomination: 'PHALDUXHA'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALDUXHA'.

The new *Phalaenopsis* plant is a product of a planned breeding program conducted by the inventor in Bleiswijk, The Netherlands. The objective of this breeding program was to create a new *Phalaenopsis* plant with several peduncles and numerous attractive and unique white flowers, suitable for potted plant production.

The new *Phalaenopsis* plant 'PHALDUXHA' is a result of cross-pollination made by the inventor in October 2005 in Bleiswijk, The Netherlands of the proprietary female, or seed parent, *Phalaenopsis* hybrid '23266-0002' (unpatented) with the proprietary male, or pollen parent, *Phalaenopsis* hybrid '11968-0004' (unpatented).

The new *Phalaenopsis* was selected by the inventor as a single plant within the progeny of the stated cross-pollination in a controlled greenhouse in Bleiswijk, The Netherlands in January 2009. Asexual reproduction of the new *Phalaenopsis* plant by meristem tissue culture since 2011 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Sep. 24, 2015. 'PHALDUXHA' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALDUXHA' as a new and distinct variety of *Phalaenopsis* plant.

1) White flowers;
2) 1 to 4 peduncles;
3) Peduncle is long and sturdy; and
4) Shape of the leaf is obovate.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 40-week old plants in January 2016. Colors in the photographs may differ from the color values cited in the detailed botanical description, which accurately describe the actual colors of the new variety.

DESCRIPTION OF THE NEW VARIETY

Figure 1:
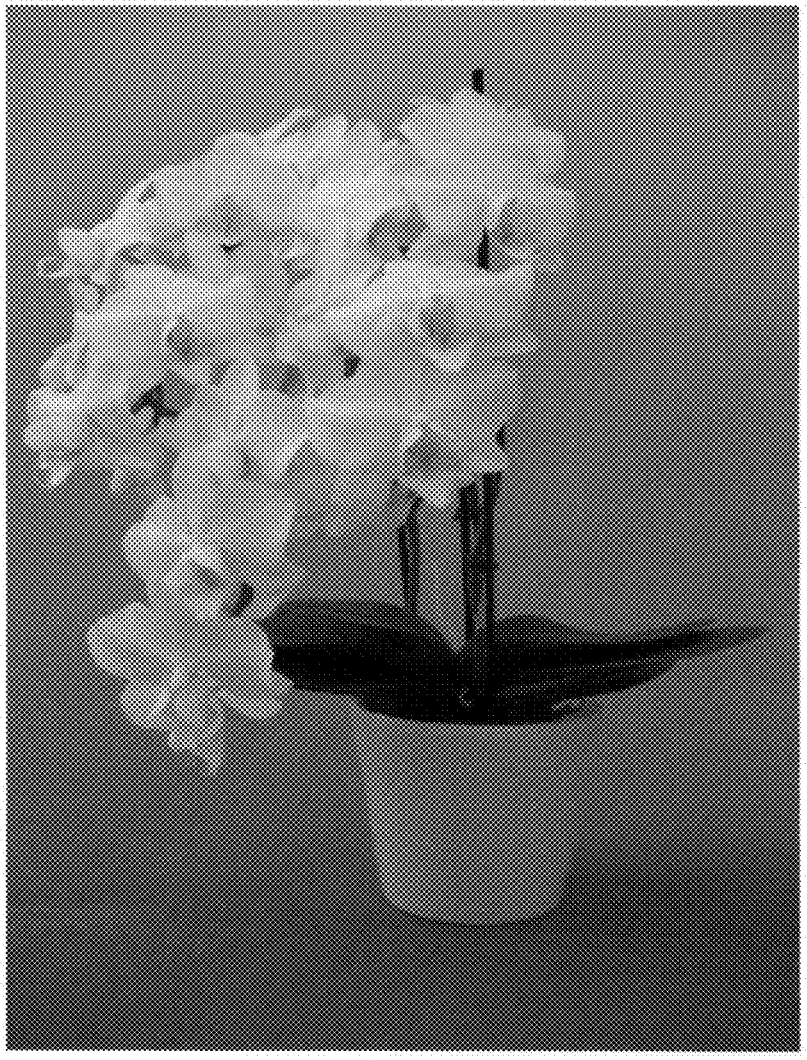
FIG. 1 shows the overall plant habit, including blooms and foliage of 'PHALDUXHA'.
Figure 2:
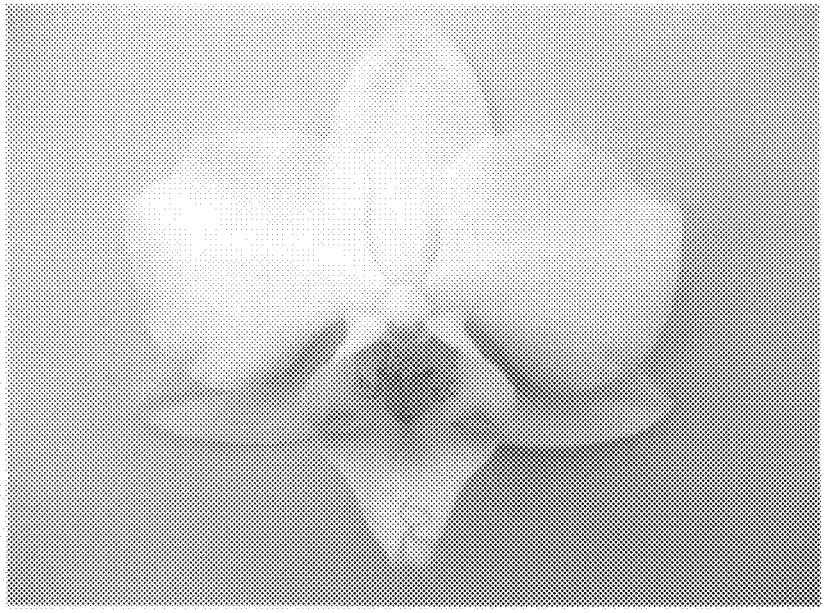
FIG. 2 shows a close-up of a flower of 'PHALDUXHA'.
Figure 3:
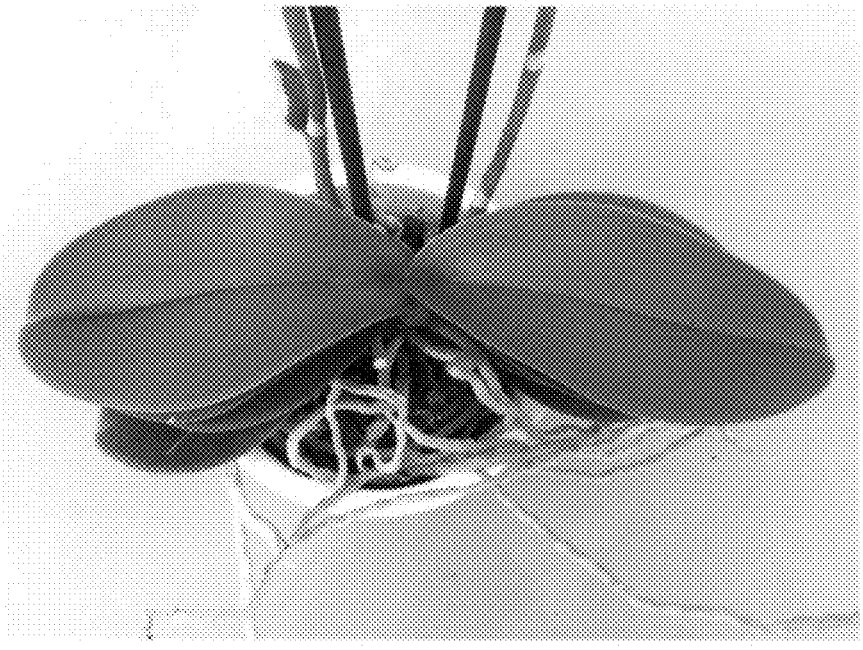
FIG. 3 shows a close-up of the leaves of 'PHALDUXHA'.

The following detailed description sets forth the distinctive characteristics of 'PHALDUXHA'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in January 2016 on 40-week old plants which were planted from a nursery tray in 9 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:
- *Family*.—Orchidaceae.
- *Botanical*.—*Phalaenopsis* hybrid.
- *Common name*.—Moth orchid.
- *Variety name*.—'PHALDUXHA'.

Parentage:
- *Female parent*.—*Phalaenopsis* cultivar '23266-0002' (unpatented).
- *Male parent*.—*Phalaenopsis* cultivar '11968-0004' (unpatented).

Propagation:
- *Type*.—Meristem tissue culture.

Roots:
- *Root description*.—Greyed-green colored roots with lateral roots having light green colored root tips.

Plant:
- *Commercial crop time to flowering*.—Approximately 38 to 40 weeks from a rooted cutting to finish in a 9 cm pot.
- *Growth habit of peduncle*.—Standard, green leaves, raceme to panicle.
- *Height (from soil level to top of inflorescence)*.—Approximately 24.0 cm to 34.0 cm.
- *Width (measured from leaf tips)*.—About 22.0 cm to 27.0 cm.
- *Vigor*.—Strong.

Leaves:
- *Mature leaves*.—Quantity per plant: 10 to 12 leaves are produced before flowering. Length (fully expanded): 12.0 cm to 15.0 cm. Width: 7.0 cm to 8.0 cm. Shape: Obovate. Base shape: Slightly elongated. Apex: Rounded unequal. Leaf blade angle with the petiole (measured from the horizontal position): Between 0 degrees and 25 degrees. Leaf margin: Entire. Color: Upper surface: RHS 147A; towards the base RHS 146A. Lower surface: RHS 146B. Texture: Rough. Thickness: 2.9 mm to 3.1 mm. Venation: Pattern: Parallel. Color of the midvein: Upper surface: RHS 147A. Lower surface: RHS 146A.

Peduncle:
- *Quantity per plant*.—1 to 4.
- *Number of flowers per peduncle*.—10 to 14.
- *Length*.—25.0 cm to 30.0 cm.
- *Diameter*.—4.2 mm to 4.6 mm.
- *Strength*.—Strong.
- *Aspect*.—Upright to pendant.
- *Texture*.—Smooth.
- *Color*.—Green (RHS 146B) with a touch of greyed-brown (RHS N199A).
- *Internode length*.—20.0 mm to 30.0 mm.
- *Callosities*.—None.

Inflorescence description:
- *Appearance*.—Upright to slightly pendant, raceme to panicle inflorescence with bilaterally symmetrical flowers that open in succession beginning with the lowermost flower.
- *Inflorescence size*.—Height (from base to tip): 130.0 mm to 150.0 mm.
- *Flowering time*.—First flowers can be expected 7 to 8 months after planting in a 9 cm pot.
- *Flower*.—Height: 48.0 mm to 53.0 mm. Diameter: 58.0 mm to 63.0 mm. Depth of lip: 17.0 mm to 19.0 mm.
- *Flower longevity*.—On the plant: 8 to 12 weeks.
- *Fragrance*.—Absent.
- *Flower bud*.—Average size: Medium. Length: 19.0 mm to 21.0 mm. Width: 13.0 mm to 15.0 mm. Shape: Egg shaped. Color: Light green (RHS 145B).
- *Petals*.—Arrangement: Open/free. Shape: Semi-circular. Apex: Obtuse asymmetric. Margin: Entire. Length (from base to tip): 28.0 mm to 30.0 mm. Width: 27.0 mm to 29.0 mm. Color (when fully opened): Upper surface: Basic color: White (RHS 155C). Over color: Absent. Lower surface: Basic color: White (RHS 155C). Over color: Light green at the base (RHS 145D).
- *Dorsal sepal*.—Shape: Elliptic. Apex: Obtuse symmetric. Margin: Entire. Length (from base to tip): 27.0 mm to 29.0 mm. Width: 16.0 mm to 18.0 mm. Color (when fully opened): Upper surface: Basic color: White (RHS 155C). Over color: Absent. Lower surface: Basic color: White (RHS 155C). Over color: Light green (RHS 145D) diluted toward the apex.
- *Lateral sepals*.—Shape: Ovate. Apex: Obtuse asymmetric. Margin: Entire. Length (from base to tip): 32.0 mm to 34.0 mm. Width: 17.0 mm to 19.0 mm. Color (when fully opened): Upper surface: Basic color: White (RHS 155C). Over color: Diluted yellow-green (RHS 145D) on one side. Lower surface: Basic color: White (RHS 155C). Over color: Yellow-green (RHS 145D) on lower side.
- *Labellum (lip)*.—Margin: Entire. Whiskers: Present. Length of whiskers: 19.0 mm to 21.0 mm. Color of whiskers: White (RHS 155C). Pubescence on the lip: Absent.
- *Lateral lobe*.—Shape: Spatulate. Length (from base to tip): 18.0 mm to 20.0 mm. Width: 13.0 mm to 15.0 mm. Color: White (RHS 155C) and green-yellow (RHS 151A and 1B) on one side, with red-purple dots (RHS 71A) towards the callus.
- *Apical lobe*.—Shape: Triangular/trullate. Length: 17.0 mm to 19.0 mm. Width: 19.0 mm to 21.0 mm. Color: White (RHS 155C) and green-yellow (RHS 151A and 1B) at the base.
- *Callus*.—Average size: Medium. Height: 0.5 cm to 0.7 cm. Length: 0.5 cm to 0.7 cm. Width: 0.4 cm to 0.6 cm. Color: Yellow (RHS 2B) with very small dots.

*Reproductive organs*.—Column: Length: 7.0 mm to 9.0 mm. Diameter: 2.7 mm to 3.0 mm. Color: White (RHS 155C). Pollinia: Quantity: 2. Diameter: 1.0 mm to 1.2 mm. Color: Orange (RHS 26A). Ovary (part of pedicel with small ribs towards the column): Length: 8.0 mm to 10.0 mm. Diameter: 2.1 mm to 2.3 mm. Pedicel: Length: 29.0 mm to 31.0 mm. Diameter: 2.4 mm to 2.6 mm. Color: Green (RHS 147A), becoming lighter (RHS 145A to 145C) towards the flower.

Disease, pest, and stress resistance: No specific resistance or susceptibility observed, to pathogens and pests common to *Phalaenopsis*.

Fruit and seeds: Fruit and seed development has not been observed on plants of the new *Phalaenopsis* to date.

COMPARISON WITH PARENTAL AND COMMERCIAL VARIETIES

The female parent of 'PHALDUXHA', *Phalaenopsis* cultivar '23266-0002' (unpatented), is no longer in existence so a meaningful comparison cannot be made.

'PHALDUXHA' differs from male parent plant '11968-0004' (unpatented) in that 'PHALDUXHA' has strong curvature of the lateral lobe, whereas '11968-0004' has medium curvature of the lateral lobe. Additionally, 'PHALDUXHA' has longer whiskers and wider flowers than '11968-0004'.

'PHALDUXHA' is most similar to the commercial *Phalaenopsis* plants named 'PHALBAPAK' (U.S. Plant Pat. No. 27,508) and 'ANTWAREN' (unpatented). 'PHALDUXHA' differs from the commercial variety 'PHALBAPAK' in that 'PHALDUXHA' has sepals with lower surfaces that have light green over color, petals with an obtuse apex, and a lateral lobe of the lip that is dotted at the base, whereas 'PHALBAPAK' has sepals with lower surfaces that have light purple over color, petals with a rounded apex, and a lateral lobe of the lip that is striped at the base. Additionally, 'PHALDUXHA' has narrower petals than 'PHALBAPAK'.

'PHALDUXHA' differs from the commercial variety 'ANTWAREN' in that 'PHALDUXHA' has petals with an obtuse apex and medium callus, whereas 'ANTWAREN' has petals with a rounded apex and small callus. Additionally, 'PHALDUXHA' has longer whiskers than 'ANTWAREN'.

I claim:

1. A new and distinct variety of *Phalaenopsis* plant named 'PHALDUXHA', substantially as described and illustrated herein.

* * * * *